(12) United States Patent
Watanabe

(10) Patent No.: US 6,315,726 B1
(45) Date of Patent: Nov. 13, 2001

(54) ULTRASONIC DIAGNOSIS APPARATUS

(75) Inventor: Yoshinobu Watanabe, Yokohama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/580,198

(22) Filed: May 26, 2000

(30) Foreign Application Priority Data

Aug. 30, 1999 (JP) .................................................. 11-243917

(51) Int. Cl.[7] .......................................................... A61B 8/00
(52) U.S. Cl. ............................................. 600/447; 600/443
(58) Field of Search .................................... 600/403, 444, 600/447, 449, 454, 455; 128/916

(56) References Cited

U.S. PATENT DOCUMENTS

| | | |
|---|---|---|
| 5,839,442 | 11/1998 | Chiang et al. . |
| 6,104,673 | * 8/2000 | Cole et al. ............................. 367/138 |
| 6,123,671 | * 9/2000 | Miller ................................... 600/447 |
| 6,126,603 | * 10/2000 | Hatfield et al. ....................... 600/454 |

FOREIGN PATENT DOCUMENTS

| | | |
|---|---|---|
| 5-228139 | 9/1993 | (JP) . |
| 6-225874 | 8/1994 | (JP) . |

* cited by examiner

Primary Examiner—Marvin M. Lateef
Assistant Examiner—Maulin Patel
(74) Attorney, Agent, or Firm—Louis Woo

(57) ABSTRACT

In an ultrasonic diagnosis apparatus, the circuitry is divided into two parts, that is, first and second units which are connected with a cable. The first unit includes a trigger signal generation circuit for generating a trigger signal in response to a command signal, an ultrasonic wave transmitting and receiving circuit including a probe for transmitting ultrasonic waves in response to the trigger signal and receiving reflected ultrasonic waves to generate a reception signal. The cable transmits the reception signal and the trigger signal. The second unit includes a clock signal generation circuit for generating a clock signal in response to the trigger signal transmitted through the cable, and a/d converter for a/d converting the received reflected ultrasonic waves in response to the clock signal to output ultrasonic diagnosis data. A frequency difference detection circuit for detecting a frequency error between the clock signal and a reference frequency signal and a compensating circuit for compensating the ultrasonic diagnostic data to output compensated ultrasonic diagnostic data may be further provided.

3 Claims, 6 Drawing Sheets

ULTRASONIC DIAGNOSIS APPARATUS

BACKGROUND OF THE INVENTION

1. Field of the Invention

This invention relates to an ultrasonic diagnosis apparatus for providing ultrasonic diagnostic image data.

2. Description of the Prior Art

An ultrasonic diagnosis apparatus for providing ultrasonic image data having independent cases is known. Japanese patent application provisional publication No. 5-228139 and No. 6-225874 disclose the independent case type of ultrasonic diagnosis apparatus.

FIG. 5 is a block diagram of a prior art ultrasonic diagnosis apparatus disclosed in Japanese patent application provisional publication No. 5-228139. In this ultrasonic diagnosis apparatus, the whole unit is divided into the main body 1 and an operation unit 2 which are electrically connected to each other with connection cables. An operation panel 4 and a display monitor 5 are provided to the operation unit 2 to which an ultrasonic wave probe 3 is connected. The main body 1 and the operation unit 2 can be independently moved.

FIG. 6 is a block diagram of another prior art ultrasonic diagnosis apparatus disclosed in Japanese patent application provisional publication No. 6-225874. In this ultrasonic diagnosis apparatus, the whole circuitry is divided into two parts. The first case having a compact size is arranged near the person to be diagnosed. On the other hand, the second case having a large scale of circuitry necessary for high performance diagnosis is remotely arranged. Thus, digital data transmission is effected between both cases with a fiber optic cable.

SUMMARY OF THE INVENTION

The aim of the present invention is to provide a superior ultrasonic diagnosis apparatus.

In an ultrasonic diagnosis apparatus, the circuitry is divided into two parts, that is, first and second units which are connected with a cable. The first unit includes a trigger signal generation circuit for generating a trigger signal in response to a command signal, an ultrasonic wave transmitting and receiving circuit including a probe for transmitting ultrasonic waves in response to the trigger signal and receiving reflected ultrasonic waves. The cable transmits the received reflected ultrasonic waves and the trigger signal. The second unit includes a clock signal generation circuit for generating a clock signal in response to the trigger signal transmitted through the cable, and an a/d converter for a/d converting (sampling) the received reflected ultrasonic waves in response to the clock signal to output ultrasonic diagnosis data. A frequency difference detection circuit for detecting a frequency error between the clock signal and a reference frequency signal may be further provided. A compensating circuit may compensate the ultrasonic diagnostic data to output compensated ultrasonic diagnostic data.

BRIEF DESCRIPTION OF THE DRAWINGS

The object and features of the present invention will become more readily apparent from the following detailed description taken in connection with the accompanying drawings in which.

The same or corresponding elements or parts are designated with like references throughout the drawings.

DETAILED DESCRIPTION OF THE INVENTION

First Embodiment

Figure 1:
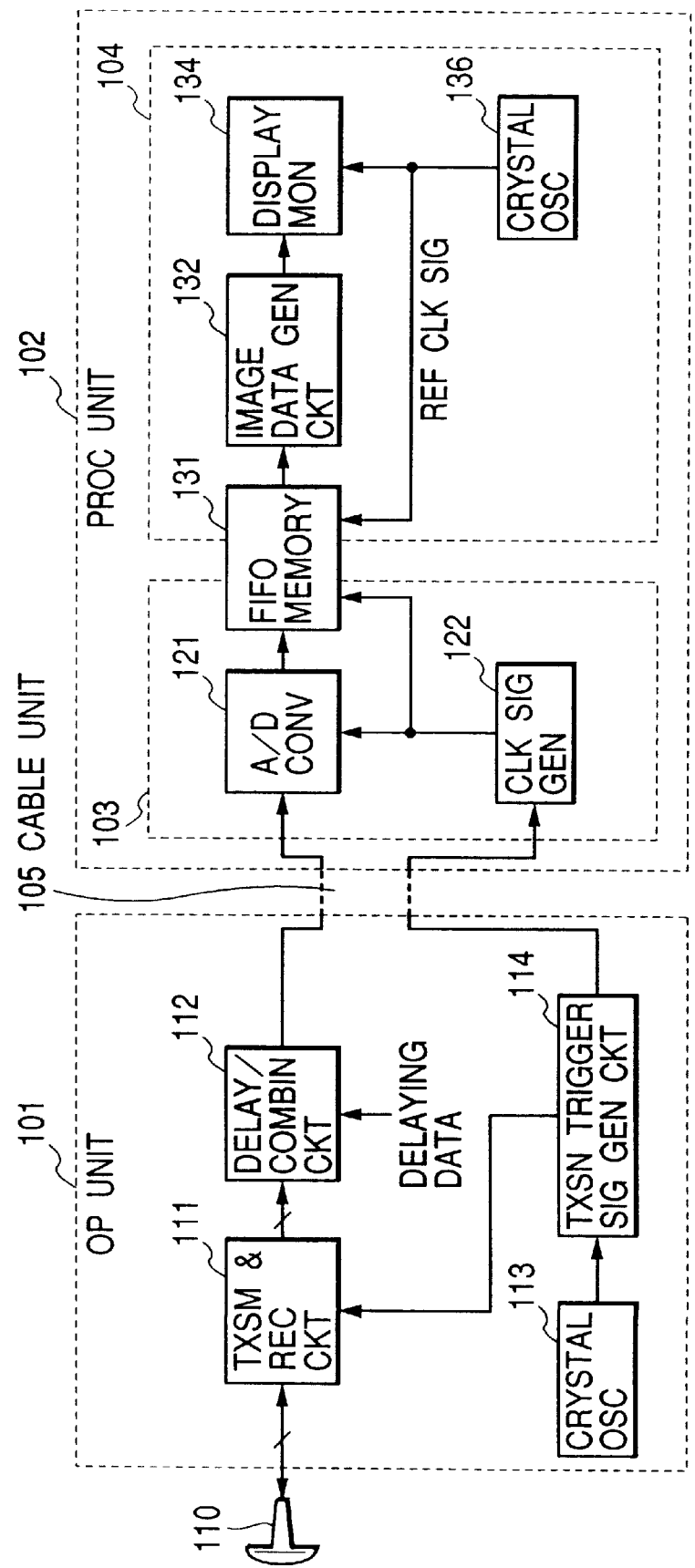
FIG. 1 is a block diagram of an ultrasonic diagnosis apparatus according to a first embodiment of this invention.

FIG. 1 is a block diagram of an ultrasonic diagnosis apparatus according to a first embodiment of this invention.

The ultrasonic diagnosis apparatus includes a probe 110, an operation unit 101, a cable unit 105, and a processing unit 102.

The probe 110 includes a plurality of ultrasonic vibration elements arranged in an array.

The operation unit 101 is coupled to the processing unit 102 with the cable unit 105 to independently locate the operation unit 101 and the processing unit 102. That is, the operation unit 101 is located adjacent to the human body subjected to the diagnosis. On the other hand, the processing unit 102 can be remotely arranged.

The operation unit 101 includes a crystal oscillator 113 for generating a first clock signal, a trigger signal generation circuit 114 for generating a trigger signal in response to the first clock signal, a transmitting and receiving circuit 111 for generating a drive pulse in response to a trigger signal to supply the drive pulse to the probe 110, and a delaying/combining circuit for delaying respective reception components derived from a plurality of ultrasonic vibration elements and combines the delayed reception components to output a combined reception signal.

The cable unit 105 transmits the combined reception signal and the trigger signal to the processing unit 102.

The processing unit 102 includes a clock signal generation circuit 122 for generating a second clock signal, an a/d converter 121 for a/d-converting (sampling) the combined reception signal to output a digital reception signal in response to the second clock signal, a FIFO (first-in-first-out) memory 131, a crystal oscillator 136 for generating a reference clock signal, a video data processing circuit 132 for processing the combined reception signal from the FIFO memory 131 to generate display data, and a display monitor 134 for displaying the display data to provide display image for ultrasonic diagnosis to the operator.

Figure 2:
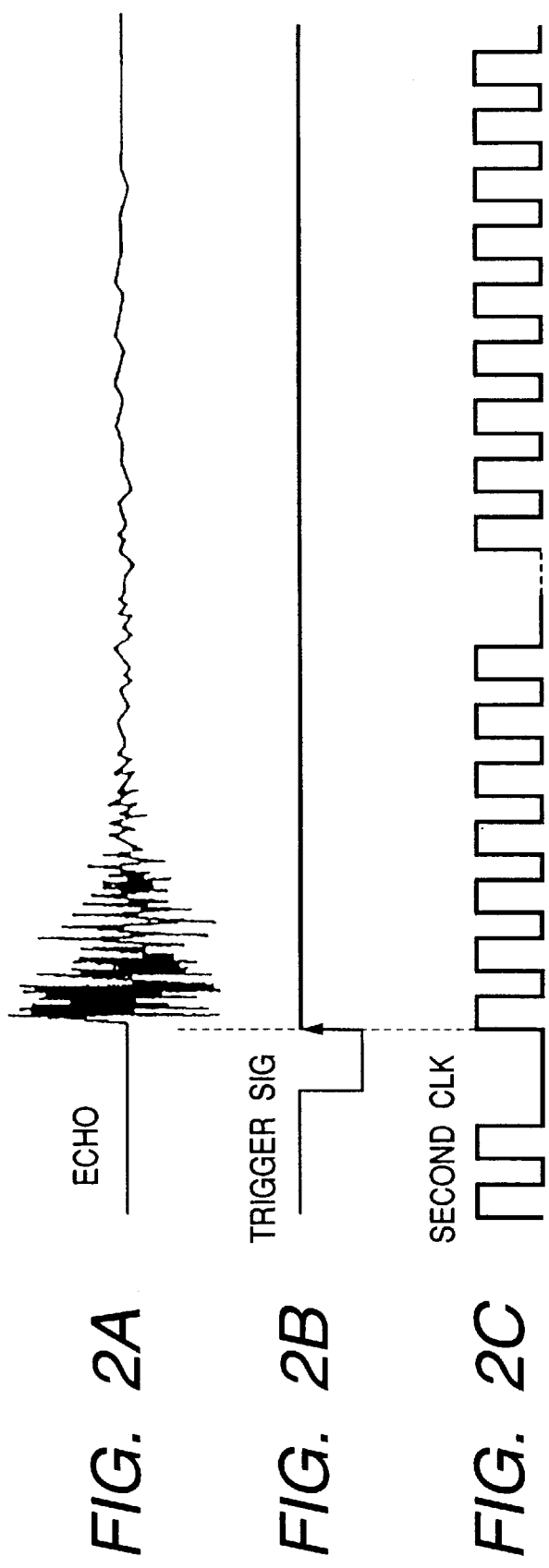
FIGS. 2A to 2C are graphical drawings showing the operation of the ultrasonic diagnosis apparatus according to the first embodiment.

FIGS. 2A to 2C are graphical drawings showing the operation of the ultrasonic diagnosis apparatus according to the first embodiment.

The trigger signal generation circuit 114 generates the trigger signal in response to the first clock signal as shown in FIG. 2B. The first clock signal is periodically generated at a desired cycle of data transmission. The transmitting and receiving circuit 111 generates the drive pulse in response to the trigger signal to supply the drive pulse to at least one of vibration elements of the probe 110. The probe 110 generates (induces) an ultrasonic wave pulse which is transmitted through the human body.

The reflected ultrasonic waves (echo signal) is received by the prove 110 as shown in FIG. 2A. More specifically, respective vibration elements receive the reflected ultrasonic wave signals (echo signals) to generate reception signals.

The delaying/combining circuit 112 delays respective reception signals derived from a plurality of ultrasonic vibration elements in accordance with delaying data for a desired directivity and combines the delayed reception signals to output the combined reception signal having the desired directivity.

The cable unit 105 transmits the combined reception signal and the trigger signal to the processing unit 102.

The clock signal generation circuit 122 is reset and started in response to the trigger signal transmitted from the operation unit 101 through the cable unit 105 as shown in FIG. 2C.

The a/d converter 121 a/d-converts the combined reception signal to output a digital reception signal in response to the second clock signal. The FIFO (first-in-first-out) memory 131 stores the digital reception signal. The FIFO memory 131 outputs the stored digital reception signal in response to the reference clock. The image data generation circuit 132 generates image data for ultrasonic diagnosis from the reception signal from the FIFO memory 131. The display monitor 134 provides a display image for ultrasonic diagnosis to the operator from the image data from the image data generation circuit 132.

The circuitry in the processing unit 102 is divided into a first block 103 and a second block 104. The storing side of the FIFO memory 131 is included in the first block 103. On the other hand, the reading side of the FIFO memory 131 is included in the second block 104. The first and second clock signals for respective blocks (including the operation unit) are independently generated. Thus, the necessity of transmitting clock signals through the cable unit 105 is eliminated, so that asynchronous operations at respective blocks are provided.

As mentioned above, according to the first embodiment, the necessity of a fiber optic cable having a high noise resistivity can be eliminated. Moreover, according to the first embodiment, the necessity of transmitting the clock signal through the cable can be eliminated.

As mentioned above, according to the first embodiment, the necessity in transmitting a clock signal for synchronous operation between respective blocks is eliminated. Accordingly, it becomes easy to extend the length of the cable.

Second Embodiment

Figure 3:
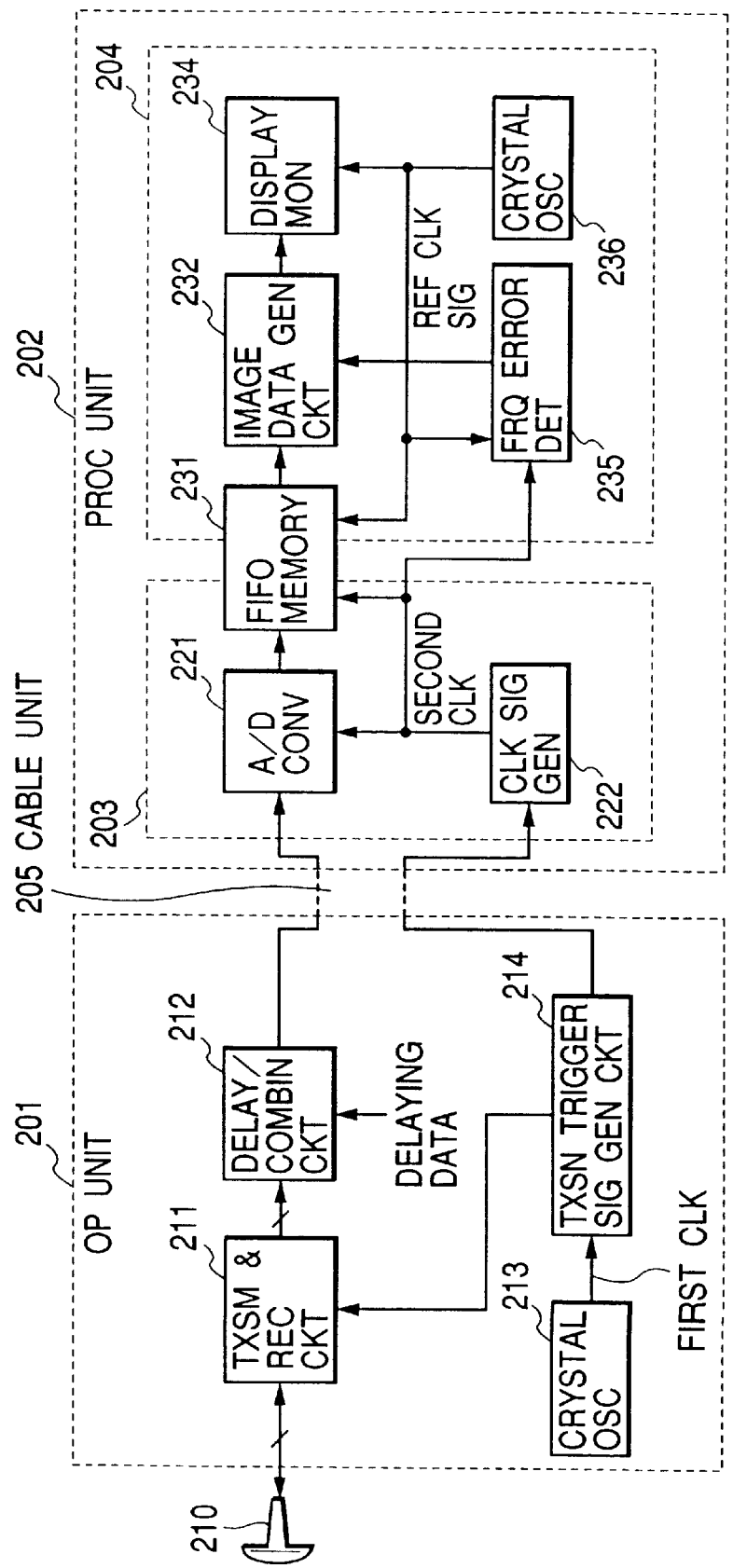
FIG. 3 is a block diagram of an ultrasonic diagnosis apparatus according to a second embodiment of this invention.

FIG. 3 is a block diagram of an ultrasonic diagnosis apparatus according to a second embodiment of this invention. FIGS. 4A to 4D are graphical drawings showing the operation of the ultrasonic diagnosis apparatus according to the second embodiment.

The structure of the second embodiment is substantially the same as the first embodiment. The difference is that a frequency error detection circuit 235 is further provided. Moreover, an image data generation circuit 132 generates the image data for diagnosis such that a frequency error between clock signals is compensated.

The clock accuracy detection and compensation circuit 235 detects difference in counts of clock pulses between the second clock signal and the reference clock signal to generate a compensation signal in accordance with the difference in counts, i.e., the frequency error. The compensation signal is supplied to an image data generation circuit 232 to compensate the image data such that error in the image displayed on the display monitor 134 due to difference in frequency between the second clock signal and the reference clock signal is compensated.

In FIG. 3, the ultrasonic diagnosis apparatus according to the second embodiment includes a probe 210, an operation unit 201, a cable unit 205, and a processing unit 202.

The probe 210 includes a plurality of ultrasonic vibration elements arranged in an array.

The operation unit 201 is coupled to the processing unit 202 with the cable unit 205 to independently locate the operation unit 201 and the processing unit 202. That is, the operation unit 201 is located adjacent to the human body subjected to the diagnosis.

The operation unit 201 includes a crystal oscillator 213 for generating a first clock signal, a trigger signal generation circuit 214 for generating a trigger signal in response to the first clock signal, a transmitting and receiving circuit 211 for generating a drive pulse in response to a trigger signal to supply the drive pulse to the probe 210 and a delaying/combining circuit for delaying respective reception components derived from a plurality of ultrasonic vibration elements and combines the delayed reception components to output a combined reception signal.

The cable unit 205 transmits the combined reception signal and the trigger signal to the processing unit 202.

The processing unit 202 includes a clock signal generation circuit 222 for generating a second clock signal, an a/d converter 221 for a/d-converting the combined reception signal to output a digital reception signal in response to the second clock signal, a FIFO (first-in-first-out) memory 231, a crystal oscillator 236 for generating a reference clock signal, a video data processing circuit 232 for processing the combined reception signal from the FIFO memory 231 to generate display data, and a display monitor 234 for displaying the display data to provide display image for ultrasonic diagnosis to the operator.

FIGS. 4A to 4D are graphical drawings showing the operation of the ultrasonic diagnosis apparatus according to the second embodiment.

Figure 4:
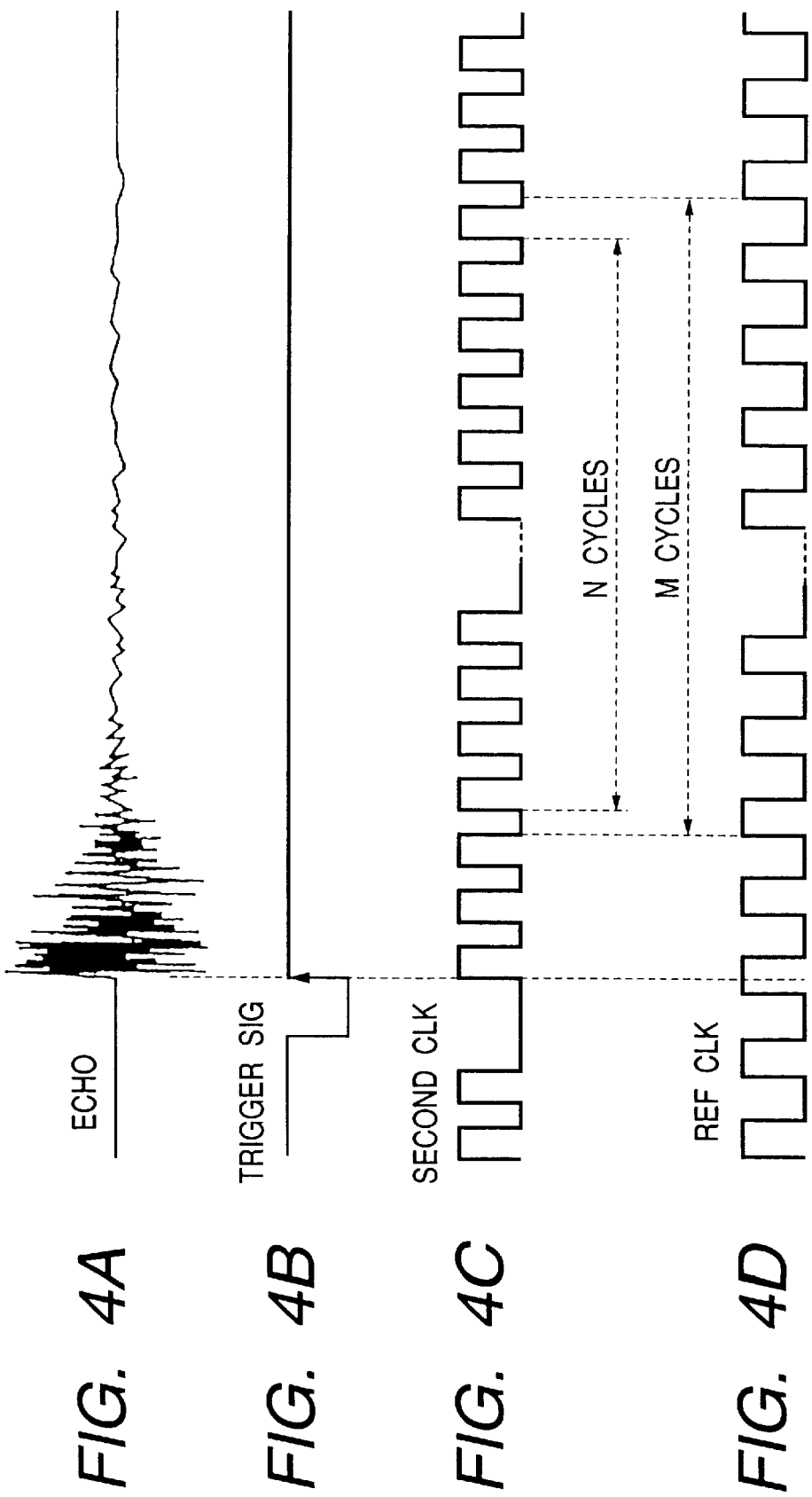
FIGS. 4A to 4D are graphical drawings showing the operation of the ultrasonic diagnosis apparatus according to the second embodiment.
Figure 5:
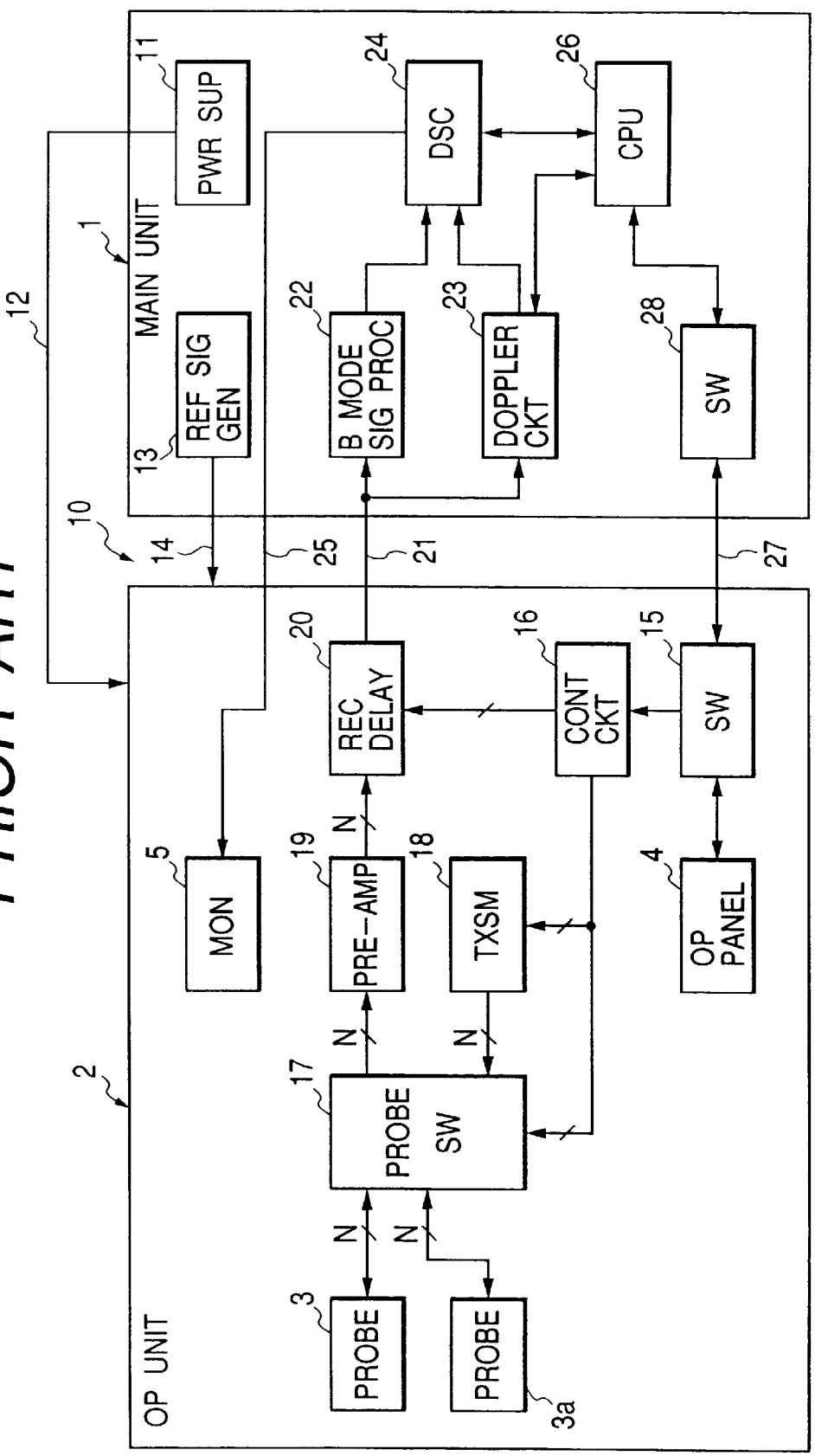
FIG. 5 is a block diagram of a prior art ultrasonic diagnosis apparatus.
Figure 6:
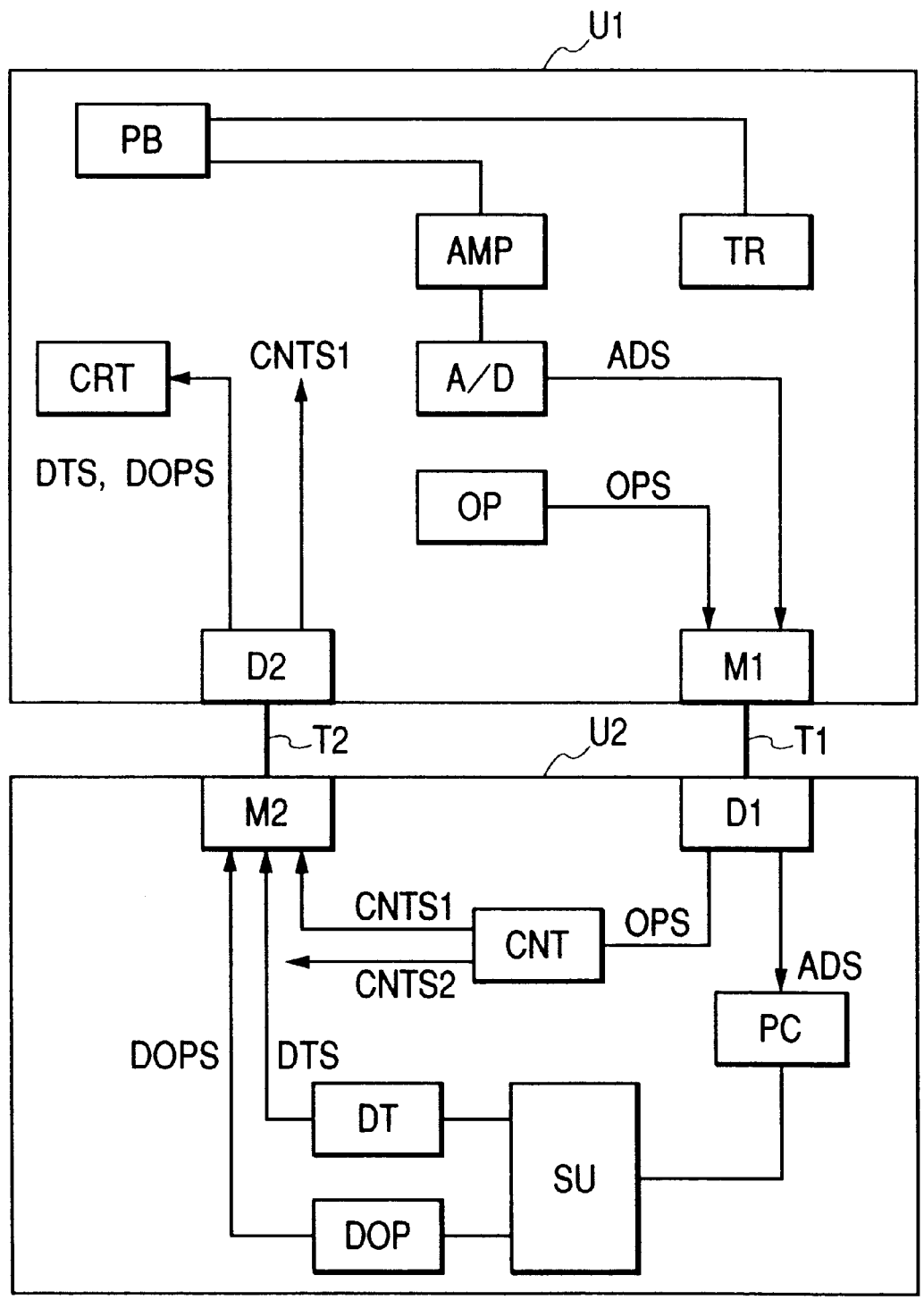
FIG. 6 is a block diagram of another prior art ultrasonic diagnosis apparatus.

The trigger signal generation circuit 214 generates the trigger signal in response to the first clock signal as shown in FIG. 4B. The transmitting and receiving circuit 211 generates the drive pulse in response to the trigger signal to supply the drive pulse to the probe 210. The probe 210 induces an ultrasonic pulse in the human body or the like.

The reflected ultrasonic waves (echo signal) is received by the prove 210 as shown in FIG. 4A. More specifically, respective vibration elements receive the reflected ultrasonic wave signals (echo signals) to generate reception signals.

The delaying/combining circuit 212 delays respective reception signals derived from a plurality of ultrasonic vibration elements in accordance with delaying data to have a desired directivity and combines the delayed reception signals to output the combined reception signal having the desired directivity.

The cable unit 205 transmits the combined reception signal and the trigger signal to the processing unit 202.

The clock signal generation circuit 222 is reset and started in response to the trigger signal transmitted from the operation unit 201 through the cable unit 205 as shown in FIG. 4C.

The a/d converter 221 a/d-converts the combined reception signal to output a digital reception signal in response to the second clock signal. The FIFO (first-in-first-out) memory 231 stores the digital reception signal. The FIFO memory 231 outputs the stored digital reception signal in response to the reference clock.

The frequency error detection circuit 235 detects a frequency error of the second clock signal (f1) from the reference clock signal (f2) as shown in FIGS. 4C and 4D. That is, the frequency error detection circuit 235 counts M pulses (cycles) in the reference clock signal from the crystal oscillator 236 and counts the pulses (N) of the second clock signal. The frequency error detection circuit 235 calculates the actual frequency as follows:

$$f1=f2 \times N/M \qquad (1)$$

In this process, there may be two counts of error between the second clock signal and the reference clock signal, the maximum frequency error is give by:

$$\Delta f=2/N \qquad (2)$$

Accordingly, it is assumed that the compensation error should be suppressed below 0.1%. M is determined such that the value N is made more than 2000.

The image data generation circuit 232 generates the image data such that error in the image data due to the frequency difference between the second clock signal and the reference signal is compensated.

The display monitor 234 displays a display image for ultrasonic diagnosis from the image data from the image data generation circuit 232 of which error due to the frequency difference is compensated.

As mentioned above, according to the second embodiment, the necessity in transmitting a clock signal for synchronous operated between respective blocks is eliminated. That is, asynchronous operation every block is provided. Accordingly, a high noise resistivity is not required in the communication cable. Moreover it becomes possible to extend the length of the cable. Moreover, it is possible to select the optimum frequency for each block, so that this eliminates the necessity of high speed responsive ICs. Moreover, the image data generation circuit 232 generates image data to draw a display image on the display monitor 234 in accordance with the frequency difference data (compensation data), so that if clock frequencies at respective clocks are different from each other, the displayed image is free from the frequency errors. In other wards, the clock signal generator 222 can be structured with a simple self-oscillation circuit, so that miniaturization can be provided and reduction in the cost is also provided.

According to the second embodiment, the necessity of using clock signals having the same frequency and the same phase between respective blocks can be eliminated.

What is claimed is:

1. An ultrasonic diagnosis apparatus comprising:
   a first unit including:
      trigger signal generation means for generating a trigger signal in response to a command signal: and
      ultrasonic wave transmitting and receiving means including a probe for including ultrasonic waves in a human body in response to said trigger signal and receiving reflected ultrasonic waves to generate a reception signal;
   transmitting means for transmitting said reception signal and said trigger signal; and
   a second unit including:
      clock signal generation means for generating a clock signal in response to said trigger signal from said transmitting means; and
      sampling means for sampling said reception signal from said transmitting means in response to said clock signal to output ultrasonic diagnosis data.

2. An ultrasonic diagnosis apparatus as claimed in claim 1, further comprising frequency difference detection means for detecting a frequency difference between said clock signal and a reference frequency signal used for processing said ultrasonic diagnosis data.

3. An ultrasonic diagnosis apparatus as claimed in claim 2, further comprising compensating means for compensating said ultrasonic diagnostic data in accordance with said detected frequency difference to output compensated ultrasonic diagnostic data.

* * * * *